United States Patent
He et al.

[11] Patent Number: 5,817,609
[45] Date of Patent: Oct. 6, 1998

[54] BAR COMPOSITION COMPRISING LOW VISCOSITY OILS PRE-THICKENED BY NON-ANTIFOAMING HYDROPHOBIC POLYMERS

[75] Inventors: Mengtao He, Wayne, N.J.; Michael Massaro, Congers, N.Y.; Gregory McFann, East Rutherford, N.J.; Liang Sheng Tsaur, Norwood, N.J.; Gail Beth Rattinger, Teaneck, N.J.; Michael Paul Aronson, West Nyack, N.Y.

[73] Assignee: Lever Brothers Company, Division of Conopco, Inc., New York, N.Y.

[21] Appl. No.: 779,548

[22] Filed: Jan. 8, 1997

[51] Int. Cl.⁶ ............................... A61K 7/50; C11D 9/22
[52] U.S. Cl. .................. 510/133; 510/130; 510/131; 510/139; 510/141; 510/157; 510/156
[58] Field of Search ................... 510/130, 131, 510/133, 141, 152, 155, 139, 156

[56] References Cited

U.S. PATENT DOCUMENTS

| | | | |
|---|---|---|---|
| 3,814,698 | 6/1974 | Ferrara | 510/152 |
| 3,857,960 | 12/1974 | Mackles | 510/789 |
| 4,673,525 | 6/1987 | Small et al. | 510/151 |
| 4,812,253 | 3/1989 | Small et al. | 510/151 |
| 5,096,608 | 3/1992 | Small et al. | 510/153 |
| 5,154,849 | 10/1992 | Visscher et al. | 510/150 |
| 5,221,534 | 6/1993 | DesLauriers et al. | 424/78.03 |
| 5,264,144 | 11/1993 | Moroney et al. | 510/151 |
| 5,264,145 | 11/1993 | French et al. | 510/151 |
| 5,308,526 | 5/1994 | Dias et al. | 510/159 |
| 5,312,559 | 5/1994 | Kacher et al. | 510/151 |
| 5,523,017 | 6/1996 | Moran et al. | 510/447 |
| 5,547,602 | 8/1996 | Schuler | 510/152 |

FOREIGN PATENT DOCUMENTS

| | | |
|---|---|---|
| 94/01084 | 1/1994 | WIPO . |
| 94/01085 | 1/1994 | WIPO . |
| 95/26710 | 10/1995 | WIPO . |
| 96/17591 | 6/1996 | WIPO . |
| 96/17592 | 6/1996 | WIPO . |
| 96/25144 | 8/1996 | WIPO . |

OTHER PUBLICATIONS

Derwent Abstract WO 94/17166 (Aug. 1994).
Derwent Abstract WO 92/08444 (May 1992).
Derwent Abstract EP 578,481 (Jan. 1994).
Soap/Cosmetics/Chemical Specialties, Feb., 1996, p. 24.

*Primary Examiner*—Anthony Green
*Attorney, Agent, or Firm*—Ronald A. Koatz

[57] ABSTRACT

The present invention relates to personal wash bar compositions comprising hydrophobic, low viscosity (less than 1000 cp) emollient agents which have been specifically pre-thickened with defined polymer composition. Use of the specific thickeners allow incorporation of the low viscosity oil (viscosity less than 1000 cp) in the personal wash compositions to deliver enhanced skin benefits and desired user properties without compromising foaming and bar processing.

27 Claims, No Drawings

BAR COMPOSITION COMPRISING LOW VISCOSITY OILS PRE-THICKENED BY NON-ANTIFOAMING HYDROPHOBIC POLYMERS

FIELD OF THE INVENTION

The present invention relates to personal cleansing bar compositions comprising thickened low viscosity oils as moisturizing agents. More specifically, by thickening these low viscosity oils (i.e., oils having viscosity less than 1000 centipoise (cp)) with specific, oil mixable, hydrophobic polymers having a low degree of crystallinity, it is possible to deliver higher amounts of the oil to the skin/substrate from skin cleanser compositions without sacrificing foaming benefits. In this way, the advantages of these low viscosity oils can be effectively delivered. In addition, the oils thickened with these specific polymer compositions in bars were found to form large size droplets when contacted with water. Again, large size droplets are greatly advantageous for deposition and delivery of the oil to the substrate (e.g., skin) from a personal skin cleansing product.

BACKGROUND OF THE INVENTION

Personal cleansing products which can deliver skin benefit to the skin (e.g., moisturization) are highly desirable. This is generally accomplished by ensuring that a sufficient amount of effective skin benefit agent is deposited on the skin during the skin cleaning process.

One particularly desirable group of skin benefit agents are the low viscosity (less than 1000 centipoise), hydrophobic emollient oils, such us sunflower oil and mineral oil (see Table 1 herein). These oils are substantive to the skin and are generally used as moisturizers. Higher viscosity oils are also beneficial, but if one is limited to use of only higher viscosity oils, the advantages of a vast array of skin benefit agents is simply lost.

Although many lower viscosity emollient oils (i.e. see Table 1) can be added to the skin in "leave-on" type products (e.g., skin cream, moisturizer and lotion), they cannot be applied readily as aqueous-based skin cleansing compositions (e.g., surfactant containing personal wash compositions, such as shower gel and body wash liquid) because the non-thickened, low viscosity oils cause antifoaming (foaming is a strongly desired consumer attribute in cleansing compositions). Further, the non-thickened, low viscosity oils tend to be present as small size droplets which do not readily deposit onto the skin and "deliver" the benefit agent. Finally, inclusion of low viscosity emollient oils in bar may lead to processing difficulties. The low viscosity oil can readily cause phase separation from the bulk of the bar composition in the molten state at high temperature (70° C.–120° C.) during the mixing stage. A low viscosity emollient agent, such as 5% by wt. mineral oil, promotes the formation of soft, sticky material that makes the processing (i.e., chill-rolling, extrusion and stamping) of bars very difficult.

To overcome the disadvantages of the non-thickened low viscosity oils (anti-foaming, small droplets, and processing difficulties), one can attempt to thicken them before adding them to a skin cleansing bar formulation. However, most of the thickeners used for this purpose (e.g., crystalline thickeners such as paraffins, polyethylene waxes and aluminum stearate) are themselves highly anti-foaming.

It is, therefore, a tremendous challenge to find a way of thickening low viscosity hydrophobic emollient oils in personal wash compositions without sacrificing foam/lather performance or colloidal stability. A thickener which does not antifoam or destabilize would also promote the formation of larger oil droplets which could be more readily deposited/delivered to the skin during a skin cleansing process.

Techniques of delivering hydrophobic skin benefit agents from personal cleansing bars to the skin are reported in the prior art.

World patent applications WO 94/01084 and WO 94/01085 (assigned to Proctor & Gamble Co.) teach a stable and mild soap personal cleansing and moisturizing composition that can deliver hydrophobic skin benefit agents on the skin. In order to deliver efficient deposition, however, these patent applications show that the droplet size of the skin benefit agents in the cleansers has to be large (i.e., the petrolatum used has particle size between 45 and 120 micrometers and viscosity between 60,000 to 400,000 cps). In contrast to the criticality of the subject invention, the referred patent applications do not teach or suggest thickening low viscosity hydrophobic oils (i.e., viscosity below 1000 cp) in a skin cleansing formulation in order to enhance skin benefits while at the same time avoiding significant antifoaming.

World patent applications WO 95/26710, WO 96/17591, WO 96/17592, and WO 96/25144 (assigned to Proctor & Gamble Co.) teach the delivery of hydrophobic lipid ingredients from personal cleansing bars and liquids to provide skin moisturizing benefit. The lipid ingredients (5 to 40% total composition) broadly claimed are hydrophobic materials selected from (a)hydrocarbons and waxes, (b) silicones and (c) different types of esters and have a viscosity in the range of 1000 to 500,000 cp. The referred patent applications, alone or in combination, do not teach or suggest the art of thickening low viscosity hydrophobic oils (i.e., viscosity below 1000 cp) in a skin cleansing formulation to enhance the skin benefits without sacrificing the lather performance. Also, the referred applications (e.g., WO 95/26710, Page 6, Line 5–7 and WO 96/25144, Page 14, Line 21–27) do not recognize the importance of using non-crystalline lipids to reduce the antifoaming effect; thus, paraffins and other crystalline waxes (which acts effectively all as antifoamers if used together with low viscosity emollient oils) are suggested in the same category with microcrystalline waxes and petrolatum (which cause much less antifoaming if combined with low viscosity oils). In contrast, the subject invention teaches the art how to formulate low viscosity emollient oils (viscosity below 1000 cp) thickened by a specific group of hydrophobic, oil-miscible polymers with a low degree of crystallinity in personal washing formulations. It further teaches enhancing the delivery of the low viscosity oils to the skin without sacrificing the lather performance. In the subject invention, crystalline waxes such as paraffins and polyethylene are specifically excluded from the oil thickeners used.

World patent application WO 92/08444 (assigned to Proctor & Gamble Co.) teaches a mild cleansing bar composition comprising 0.5 to 20% of a hydrophobic silicone component consisting of (A) silicone gum (viscosity greater than 600,000) and (B) silicone fluid with a viscosity between 5 to 600,000. The referred patent application only teaches the mixing of one specific type of hydrophobic emollients (i.e., polydimethylsiloxanes of low viscosity, (B)) with the same type of emollient oils of higher viscosity (i.e., PDMS, (A)) to promote desired skin feel and mildness. In contrast, in order to achieve synergistic skin benefits, the subject invention teaches the art how to thicken a broad range of low viscosity (less than 1000 cp) oils using specific polymer thickeners which are structurally completely different than the PDMS, or how to thicken a broad range of low viscosity, non-silicone oils using hydrophobic, high viscosity silicone oil. As such, low viscosity oils and thickeners which have a completely different structure than the low viscosity oils together provide synergistic benefits to the skin, and as such, the mixture of low viscosity and high viscosity silicones claimed by the referred application is clearly different than the thickened oils claimed by the subject invention.

World patent application WO 94/17166 teaches a cleansing composition comprising insoluble nonionic oil or wax or mixture of oil and/or wax (3 to 40% total composition) for providing a skin benefit from the claimed cleanser composition. Applicants have found that wax in oils function as a antifoaming agent and use of such waxes as thickening agents is specifically disclaimed by the subject invention. Also, in contrast to the criticality of the subject invention, the referred patent applications do not teach or suggest thickening low viscosity hydrophobic oils (i.e., viscosity below 1000 cp) in a skin cleansing formulation to enhance the skin benefits without antifoaming.

European patent application EP 578481 (assigned to Colgate Palmolive) teaches a soap composition comprising 93 to 99.5% fatty acid soap and 0.5 to 7% water insoluble silicone with viscosity of between 20,000 and 200,000 cp. Unlike the subject invention, the referred patent application does not teach or suggest thickening low viscosity hydrophobic oils (i.e., viscosity below 1000 cp) in a skin cleansing bar to enhance the skin benefits without antifoaming.

U.S. Pat. No. 3,857,960 to L. Mackles teaches a "toilet oil bar" composition comprising 70–85% mineral oil, 5–30% monoethanolamine stearic acid amide and N, N' distearoyl ethylenediamine as solidification agents, and 1–10% non-ionic and anionic surfactants as emulsification agents. Unlike the composition of the subject invention, the referred "oil bar" does not deliver foam (see referred patent, column 1, line 21–23) but provides a white emulsion during a skin wash. Also the amide components (monomeric molecules) claimed by the referred patent are fundamentally different in molecular morphology from the polymer thickeners of the subject invention.

U.S. Pat. No. 3,814,698 to P. Ferrara teaches a milled soap composition comprising fatty acid soap and bath oil selected from isopropyl myristate, laurate esters, palmitate esters, waxes and castor oil. In contrast to the criticality of the subject invention, the referred patent applications do not teach or suggest thickening low viscosity hydrophobic oils (i.e., viscosity below 1000 cp) in a skin cleansing formulation to enhance the skin benefits without antifoaming. Specifically, the subject invention found that waxes are effective antifoaming agents in the presence of other low viscosity oils (i.e., castor oil and isopropyl myristate), and use of such waxes as thickening agents is specifically disclaimed by the subject invention.

U.S. Pat. No. 5,547,602 to W. Schuler teaches a moisturizing soap bar composition comprising 50–99% fatty acid soap, 0.5–10% petrolatum and 0.1 to 10% of emollients, such as hydroxylated milk glycerides (MP above 40° C.), etc. Unlike the subject invention, the referred patent does not teach the art of thickening low viscosity hydrophobic oils (i.e., viscosity below 1000 cp) in a skin cleansing bar to enhance the skin benefits without antifoaming.

U.S. Pat. No. 5,312,559 to Kacher et al. teaches a stable, mild soap composition comprising fatty acid soap, free fatty acid and large particle size hydrophobic petrolatum as an emollient agent. Unlike the subject invention, the referred patent does not teach the art of thickening low viscosity hydrophobic oils (i.e., viscosity below 1000 cp) in a skin cleansing bar to enhance the skin benefits without antifoaming.

The use of oils which act as benefit agents and polymers of the invention which are thickeners is also known.

U.S. Pat. No. 5,221,534 to P. DesLauriers (Pennzoil Products Company), for example, teaches health and beauty aid compositions contained in a gel comprising a mineral oil and blends of di- and tri-block copolymers based on synthetic thermoplastic rubbers. The patent teaches how to make gels that may also include other moisturizing agents. However, this patent and other literature published by Penreco (a division of Pennzoil) only teach applications of the gels in "leave-on" type products that do not contain the lather surfactants used by this invention, such as body moisturizer and lotion, and fails to teach or suggest the inclusion of the gels in any personal washing formulations containing lather surfactants.

By contrast, the subject invention is distinct in at least two important ways. First, the subject invention uses the polymer thickened oils and/or the oil/polymer blend itself as a thickener for other (same or different) low viscosity oils. Second, those oil/polymer compositions are used in personal wash compositions, not leave-on type products.

Different from leave-on type formulations (i.e., the one claimed by U.S. Pat. No. 5,221,534 which contains no lather surfactant), the personal washing bar formulations claimed by the subjective invention are fundamentally different in terms of processing and composition. Especially, the bar formulation claimed comprises at least 10% wt., preferably 25% wt. or greater the lathering surfactants. Further, the compositions of the invention will generate foam height of at least seven cm or greater after two minutes of foam aging by the Ross-Miles method (see Methodology in the Example sec.). Such foam Heights would not be generated by "leave-on" products.

Soap/cosmetics/Chemical Specialties (Page 24, February, 1996) reported a Shower-Active™ moisturizer introduced by Jergens in November, 1995. The moisturizer contains the mineral oil/polymer gels (Geahlene®) claimed by U.S. Pat. No. 5,221,534 and other ingredients, such as octyl isononanoate, steareth-2, and phosphoric acid. The moisturizer can be applied to skin in the shower to avoid the time-consuming process of applying the moisturizer after the shower. Again, however, this reference discloses the oil/polymer gels by themselves in leave-on compositions, such as body moisturizer, cream and lotion. The reference does not disclose the oil/polymer gel composition as thickeners for additional low viscosity oil (e.g., to help deposit without antifoaming) and further does not disclose the use of these polymer thickened oil compositions in personal wash compositions. Again, said "leave-on" type products comprising Geahlene® do not contain the lather surfactants used by the subjective invention to promote the lather, which is an important desired sensory cue for personal washing products.

As described in the prior art, a wide variety of hydrophobic emollient oils are desirable skin benefit agents. However, because they are antifoaming, potentially destabilizing, and do not readily deposit, low viscosity (less than 1000 cp) hydrophobic emollient agents as moisturizers are difficult to be included in personal washing formulations. Examples of such low viscosity oils include mineral oils, sunscreen oils, vegetable oils, low molecular weight lactate esters and isopropyl myristate.

While not wishing to be bound by theory, applicants believe that these low viscosity oils are emulsified easily by surfactants and thus (1) cause antifoaming and (2) are difficult to be effectively retained onto the skin during a skin cleansing (washing) process. In contrast, high viscosity oils (i.e., viscosity significantly greater than 1000 cp) are less emulsifiable and therefore form larger droplets in a cleanser, and this is desired for high foaming and oil deposition onto the skin. However, focusing on only such high viscosity oils would leave a vast array of low viscosity oils which are potentially wonderful moisturizers, but simply could not previously be effectively used.

One route for effectively depositing low viscosity oils onto the skin from a cleanser is to thicken the oils using thickening agents. It was found, however, that most conventional oil thickeners, such as paraffin wax, silica, fumed silica, silicate, and long chain fatty acid soap, all have a strong tendency to significantly depress the lather of a cleanser, especially in the presence of hydrophobic emollient oils. That is, personal wash cleanser compositions containing those thickened oils can deliver skin moisturizing benefits but fail to provide satisfactory lather performance.

In short, the prior art teaches one of two situations:

(1) personal wash compositions where low viscosity oils are thickened by known thickeners, but foaming (and/or stability) is compromised; or (2) low viscosity oils which are thickened by specific polymers (e.g., like the Pennzoil Geahlene® composition), wherein these polymer thickened oils are used in leave-on compositions for delivering the oil as a moisturizer.

Novel to the art, the subject invention formulated low viscosity emollient agents pre-thickened by a group of specific, hydrophobic, non-antifoaming polymers into skin cleansing bar formulations, and the invention provides at least three unique benefits in comparison to non-thickened low viscosity oils. First, the specific polymer thickened oils provide significantly better lather performance. Second, the thickened oils tend to form larger size droplets, which may in turn enhance the oil deposition onto skin (supported by the prior art listed above, i.e., World patent applications WO 94/01084 and WO 94/01085). Third, the specific polymer thickened oils tend to be stable in a properly-designed and processed bar formulations (see Methodology in Example Sec.), resist phase separation, and provide the proper rheological window for processing.

BRIEF SUMMARY OF THE INVENTION

Surprisingly and unexpectedly, applicants have found that it is possible to effectively thicken hydrophobic low viscosity emollient oils (viscosity less than 1000 cp) using a special group of hydrophobic polymeric thickeners, such that the low viscosity oils can be more effectively delivered from personal wash bar compositions without compromising foaming. That is, it is now possible to deliver cleansing (through surfactants), moisturization (through low viscosity oil thickened by the specific polymer compositions) and good foaming all in one personal cleansing bar composition. Also the thickened oils in bar resist phase separation and provide proper rheological window for the processing.

More specifically, the present composition comprises an aqueous-based personal wash cleanser composition comprising:

(a) 10% to 95%, preferably 25–70% by wt. of a surfactant selected from the group consisting of anionic surfactants, cationic surfactants, amphoteric surfactants, nonionic surfactants and mixtures thereof, (b) 0.5% to 45%, preferably 5% to 25% by wt. total composition a pre-thickened oil composition having a viscosity above 2000 cp, preferably above 5,000 cp, most preferably above 10,000 cp at a temperature of 25° C., wherein the pre-thickened oil composition comprises a hydrophobic emollient agent with viscosity less than 1000 cp and a thickening material that is specified in the detailed embodiment of this invention; and (c) 0.1 to 80%, preferably 5% to 75% by wt. total composition of a structuring aid and/or inert filler;

wherein the bar composition generates a foam height of seven cm or greater after two minutes of foam aging, as measured by the Ross-Miles method detailed in Methodology, Example section. "These numbers correspond to a foam height of the bar of the invention at least 30% greater than that provided by a comparative bar containing the same amount and same low viscosity oil, but where the oil has been thickened by conventional thickeners such as polyalkylene or paraffin waxes, $C_{18}$–$C_{22}$ fatty acid, fumed silica etc." These levels of foam generation differentiate the claimed skin cleansing composition from "leave-on" type skin care products, such as, for example, skin moisturizers, creams and lotions.

DETAILED DESCRIPTION OF THE INVENTION

The present invention relates to novel personal wash bar compositions which are not only able to deliver cleansing benefits normally associated with such cleansers, but are also able to deliver much higher amounts of low viscosity oil (e.g., much greater moisturization benefits) than previously possible without compromising foam attributes. Stated differently, when low viscosity oil is normally thickened (as is required to provide moisturization benefits), the thickeners which have been previously used in the art (e.g., wax) have also compromised foaming in the cleanser composition.

While low viscosity oil (i.e., mineral oil with a viscosity around 12 cp at 20° C.) has been thickened in the prior art using one of the specific polymer thickening agents selected by the subject invention (i.e, component 2, Geahlene® type compositions), the oil/polymer compositions have never previously been used in skin cleanser compositions.

Unexpectedly, however, applicants have now found that low viscosity (less than 1000 cp) oils thickened with specific polymer compositions (e.g., Geahlene® type compositions) can be used in bar compositions and permit the compositions to function as normal cleansers while providing moisturization function and without simultaneously compromising foaming. The thickened oils also resist phase separation in the bar and provide proper rheological window for the processing.

As such, the compositions of the invention will generate foam height of at least seven cm or greater after two minutes of foam aging by the Ross-Miles method (see Methodology in the Example section). Such foam generation differentiates the claimed skin cleansing bar composition from "leave-on" type skin care products, such as moisturizers, creams and lotions.

Thus, applicants have remarkably been able to obtain a desirable dual benefit (moisturizer from the low viscosity oil and improved foam) in a cleanser composition, an achievement not previously obtained in the art using low viscosity oils. Instead, the art has previously been forced to disregard a whole category of oils/benefit agents because there has previously been no suitable way to incorporate them into personal wash compositions.

The compositions of the invention comprise:
(a) 10% to 95%, preferably 25–70% by wt. of a surfactant selected from the group consisting of anionic surfactants, cationic surfactants, amphoteric surfactants, nonionic surfactants and mixtures thereof,
(b) 0.5% to 45%, preferably 5% to 25% by wt. total composition a pre-thickened oil composition having a viscosity above 2000 cp, preferably above 5,000 cp, most preferably above 10,000 cp at a temperature of 250° C.,
(c) 0.1 to 80%, preferably 5% to 75% by wt. total composition a structuring aid and/or filler.

Wherein the pre-thickened oil composition (b) comprises a hydrophobic emollient agent with viscosity less than 1000 cp and a "non-antifoaming" thickening material that is specified further below;

wherein by "non-antifoaming" is meant that a bar composition containing the polymer/oil thickening composition provides a foam height of seven cm or greater after two minutes of foam ageing, as tested by the Ross-Miles method detailed in Methodology. In contrast, a bar composition containing the same percentage of the same low viscosity oil (viscosity less than 1000 cp) which has been pre-thickened by crystalline thickeners, such as polyethylene or paraffin waxes, $C_{18}$–$C_{22}$ water insoluble fatty acid soap and fumed silica, usually provides significantly less lather (see Example Section).

Each component is further detailed below:

(a) Surfactant System
Anionic Surfactants

The anionic surfactant may be, for example, an aliphatic sulfonate, such as a primary alkane (e.g., $C_8$–$C_{22}$) sulfonate, primary alkane (e.g., $C_8$–$C_{22}$) disulfonate, $C_8$–$C_{22}$ alkene sulfonate, $C_8$–$C_{22}$ hydroxyalkane sulfonate or alkyl glyceryl ether sulfonate (AGS); or an aromatic sulfonate such as alkyl benzene sulfonate.

The anionic surfactant may also be a salt of $C_8$–$C_{22}$ carboxylic acid (or known as fatty acid soap). The fatty acid soap is known to be more irritative to skin than other mild anionic surfactants, such as sodium cocoyl isethionate. As such, the skin cleansing formulations claimed by this invention comprise less than 10% said salt of carboxylic acid.

The anionic may also be an alkyl sulfate (e.g., $C_{12}$–$C_{18}$ alkyl sulfate) or alkyl ether sulfate (including alkyl glyceryl ether sulfates). Among the alkyl ether sulfates are those having the formula:

$$RO(CH_2CH_2O)_nSO_3M$$

wherein R is an alkyl or alkenyl having 8 to 18 carbons, preferably 12 to 18 carbons, n has an average value of greater than 1.0, preferably between 2 and 3; and M is a solubilizing cation such as sodium, potassium, ammonium or substituted ammonium. Ammonium and sodium lauryl ether sulfates are preferred.

The anionic may also be alkyl sulfosuccinates (including mono- and dialkyl, e.g., $C_6$–$C_{22}$ sulfosuccinates); alkyl and acyl taurates, alkyl and acyl sarcosinates, sulfoacetates, $C_8$–$C_{22}$ alkyl phosphates and phosphates, alkyl phosphate esters and alkoxyl alkyl phosphate esters, acyl lactates, $C_8$–$C_{22}$ monoalkyl succinates and maleates, sulphoacetates, and acyl isethionates.

Sulfosuccinates may be monoalkyl sulfosuccinates having the formula:

$$R^4O_2CCH_2CH(SO_3M)CO_2M;$$

amido-MEA sulfosuccinates of the formula $$R^4CONHCH_2CH_2O_2CCH_2CH(SO_3M)CO_2M$$

wherein $R^4$ ranges from $C_8$–$C_{22}$ alkyl and M is a solubilizing cation; amido-MIPA sulfosuccinates of formula $$RCONH(CH_2)CH(CH_3)(SO_3M)CO_2M$$

where M is as defined above.

Also included are the alkoxylated citrate sulfosuccinates; and alkoxylated sulfosuccinates such as the following:

$$R-O-(CH_2CH_2O)_n\overset{\overset{O}{\|}}{C}CH_2CH(SO_3M)CO_2M$$

wherein n=1 to 20; and M is as defined above.

Sarcosinates are generally indicated by the formula $RCON(CH_3)CH_2CO_2M$, wherein R ranges from $C_8$ to $C_{20}$ alkyl and M is a solubilizing cation.

Taurates are generally identified by formula
$R^2CONR^3CH_2CH_2SO_3M$ wherein $R^2$ ranges from $C_8$–$C_{20}$ alkyl, $R^3$ ranges from $C_1$–$C_4$ alkyl and M is a solubilizing cation.

Another class of anionics are carboxylates such as follows:

$$R-(CH_2CH_2O)_nCO_2M$$

wherein R is $C_8$ to $C_{20}$ alkyl; n is 0 to 20; and M is as defined above.

Another carboxylate which can be used is amido alkyl polypeptide carboxylates such as, for example, Monteine LCQ® by Seppic.

Another surfactant which may be used are the $C_8$–$C_{18}$ acyl isethionates. These esters are prepared by reaction between alkali metal isethionate with mixed aliphatic fatty acids having from 6 to 18 carbon atoms and an iodine value of less than 20. At least 75% of the mixed fatty acids have from 12 to 18 carbon atoms and up to 25% have from 6 to 10 carbon atoms.

Acyl isethionates, when present, will generally range from about 0.5–15% by weight of the total composition. Preferably, this component is present from about 1 to about 10%.

The acyl isethionate may be an alkoxylated isethionate such as is described in Ilardi et al., U.S. Pat. No. 5,393,466, hereby incorporated by reference into the subject application. This compound has the general formula:

$$\overset{\overset{O}{\|}}{RC}-O-\overset{\overset{X}{|}}{CH}-CH_2-(O\overset{\overset{Y}{|}}{CH}-CH_2)_m-SO_3^-M^+$$

wherein R is an alkyl group having 8 to 18 carbons, m is an integer from 1 to 4, X and Y are hydrogen or an alkyl group having 1 to 4 carbons and $M^+$ is a monovalent cation such as, for example, sodium, potassium or ammonium.

Another surfactant which may be used are $C_8$ to $C_{22}$ neutralized fatty acids (soap). Preferably, the soap used are straight chain, saturated $C_{12}$ to $C_{18}$ neutralized fatty acids.

In general the anionic component will comprise from about 1 to 20% by weight of the composition, preferably 2 to 15%, most preferably 5 to 12% by weight of the composition.

Zwitterionic and Amphoteric Surfactants

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

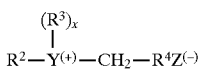

wherein $R^2$ contains an alkyl, alkenyl, or hydroxy alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-S-hexadecylsulfonio]-3-hydroxypentane-1-sulfate;
3-[P,P-diethyl-P-3,6,9-trioxatradexocylphosphonio]-2-hydroxypropane-1-phosphate;
3-[N,N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate; and
5-[N,N-di(3-hydroxypropyl)-N-hexadecylammonio]-2-hydroxy-pentane-1-sulfate.

Amphoteric detergents which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

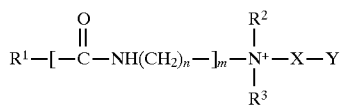

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and Y is $-CO_2-$ or $-SO_3-$ Suitable amphoteric detergents within the above general formula include simple betaines of formula:

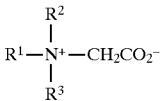

and amido betaines of formula:

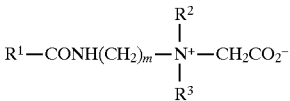

where m is 2 or 3.

In both formulae $R^1$, $R^2$ and $R^3$ are as defined previously. $R^1$ may in particular be a mixture of $C_{12}$ and $C_{14}$ alkyl groups derived from coconut so that at least half, preferably at least three quarters of the groups $R^1$ have 10 to 14 carbon atoms. $R^2$ and $R^3$ are preferably methyl.

A further possibility is that the amphoteric detergent is a sulphobetaine of formula

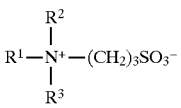

or

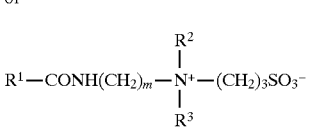

where m is 2 or 3, or variants of these in which $-(CH_2)_3SO^-_3$ is replaced by

In these formulae $R^1$, $R^2$ and $R^3$ are as discussed previously.

Amphoacetates and diamphoacetates are also intended to be covered in possible zwitterionic and/or amphoteric compounds which may be used.

The amphoteric/zwitterionic surfactant, when used, generally comprises 0% to 25%, preferably 0.1 to 20% by weight, more preferably 5% to 15% of the composition.

In addition to one or more anionic and optional amphoteric and/or zwitterionic, the surfactant system may optionally comprise a nonionic surfactant.

Nonionic Surfactants

The nonionic which may be used includes in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6-C_{22}$) phenols-ethylene oxide condensates, the condensation products of aliphatic ($C_8-C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Other surfactants which may be used are described in U.S. Pat. No. 3,723,325 to Parran Jr. and alkyl polysaccharide nonionic surfactants as disclosed in U.S. Pat. No. 4,565,647 to Llenado, both of which are also incorporated into the subject application by reference.

Preferred alkyl polysaccharides are alkylpolyglycosides of the formula $$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl units 2-, 3-, 4- and/or 6-position, preferably predominantly the 2-position.

(b) Oil/Polymer Thickening Compositions

Examples (not intended to be limiting in any way) of the types of hydrophobic emollient oils (b)(i) contemplated by the invention include as follows:

TABLE 1

Viscosity of Some Hydrophobic Emollient Oils

| Material Names | Temperatures (degree C.) Significant to Skin Cleansing | Viscosity (Centipoise, CP.) |
|---|---|---|
| Sun Flower Seed Oil | 20 | 10 |
| Mineral Oil | 20 | 12 |
| Olive Oil | 40 | 36 |
| Caster Oil | 30 | 451 |
| Oleic Acid | 30 | 26 |
| Rape Oil | 30 | 96 |
| Soybean Oil | 30 | 41 |

To thicken a low viscosity hydrophobic oil and make the thickened oil stable in a skin cleansing bar composition without sacrificing lather performance, the polymeric thickeners (b)(ii) used in this invention meet the following criteria at a temperature between 10° C. and 60° C.:

(1) hydrophobicity
a polymer or a blend of polymers that have a water solubility less than 1% by wt. in water, preferably less than 0.5% by wt. in water. The hydrophobicity is critical because the thickening agent has to be stable in the oil in the aqueous cleansing formulation;

(2) low crystallinity
a polymer or a blend of polymers which contain 80% wt or greater non-crystalline polymeric materials and less than 20% crystalline polymeric materials in a continuous matrix of the oil that it thickens.

In the subject invention, the non-crystalline polymeric materials comprise gels, amorphous solids, microcrystalline waxes and mixtures thereof. Gels and amorphous solids can be distinguished from crystalline materials by the wide-angle X-ray diffraction technique (crystalline materials provide distinct X-ray diffraction maxima, and gels and amorphous solids do not).

Microcrystalline wax is a special case. Unlike those crystalline waxes (i.e., paraffins and polyethylene), microcrystalline waxes (historically known as amorphous waxes) are of higher molecular weight, highly branched hydrocarbon chains, smaller crystalline or amophous structure (depending on the processing routes used), and much higher oil compatibility and plasticity (see: H. Bennet, Industrial Waxes, Page 89–92, published by Chemical Publishing Company, 1963, hereby included by reference into the subject application). Those unique properties and the differences between microcrystalline waxes and crystalline waxes are summarized in Table 2.

The most popular product of microcrystalline waxes is petrolatum (also known as petroleum jelly or mineral jelly), which consists of about 90% wt. a natural mixture of microcrystalline waxes plus minor amount of other impurities. Other examples of microcrystalline waxes include but are not limited to Micro. Wax, Micro. Wax 2305, Micro. Wax 1135/15W (all from Ross), and Multiwax 180M, Multiwax ML-445, Multiwax 180W, Multiwax W-445, Multiwax W-445, Multiwax W-835, Multiwax X-145 (all from Witco/Sonneborn).

TABLE 2

Major differences between microcrystalline waxes and crystalline waxes

| Major Differences | Crystalline waxes | Microcrystalline waxes |
|---|---|---|
| Manufacturing process | by pressing a paraffin wax distillate and sweating the resulting slack wax for the final oil removal. | By further solvent crystalization from the wax distillate residua. |
| Molecular Morphology | mainly straight hydro-carbons | mainly highly brached hydrocarbons |
| Molecular Weight | lower MW (i.e., 360–420). | higher MW (i.e, 580–700). |
| Crystalline Structure | large, well formed crystals (i.e., >100 microns) from wax melt or solvent. | small, irregular crystals (i.e., <5 microns) from wax melt, but amorphous materials from solvent. |
| Mechanical Properties | hard and brittle at solid state and shatter under compression, low viscosity fluid at molten state | plastic and flow under compression at gel state, viscous liquid at molten state |
| Oil Compatability | little affinity for oil | dispersable with many oils that leads to enhanced homogenous plastic mix |
| Apperance as a Film | transparent | opalescent (white, brown or black in color) |
| Thermal Contraction Coefficient (from liquid to solid or gel state) | greater | much less |

Low crystallinity is critical because a high order of crystallinity (i.e., paraffin or polyethylene waxes) in the thickened oil causes significant antifoaming;

(3) oil compatibility
a polymer or a blend of polymers which are miscible and/or dispersible in a low viscosity oil (viscosity less than 1000 cp) to form a homogenous mix that is stable in the subject liquid cleanser formulation without composition and layer separation. Oil compatibility is critical because the polymer thickener and the oil have to form a homogenous domain (i.e, thickened oil droplets) in the aqueous-based skin cleansing formulation.

Examples of the potential polymer thickeners that meet the above criteria include but are not limited to (1) rubber-based thermoplastic block copolymer, such as SEBS, SEP, SEB,
    EP, SBS, and SIS, in which
    E=polyethylene segments,
    S=polystyrene segments,
    B=polybutylene or polybutadiene segments,
    I=polyisoprene segments
    P=polypropylene segments. These copolymers are commercially available from Shell Chemical Company (under the trade name of Kraton®);

(2) silicone oil with a viscosity higher than 2000 cp, preferably higher than 5000 cp, and most preferably higher than 10,000 cp, selected from high molecular weight polydimethylsiloxanes, and other hydrophobic polydimethylsiloxane derivatives such as diethylpolysiloxane, dimethicone, C1-C30 alkyl polysiloxane. Those silicone oils are commercially available. For example, polydimethylsiloxanes of different molecular weight and viscosity are commercially available from Dow Corning under the trade name of Dow Corning 200 fluid or from General Electric under the trade name of GE silicone; and (3) Microcrystalline waxes with a viscosity higher than 2000 cp, preferably higher than 5000 cp, and most preferably higher than 10,000 cp, such as petrolatum, which is available from Ultra Chemical Inc. (tradename as Ultrapure SC or Ultrapure HMP white petrolatum) or from Fisher Scientific (Petrolatum, Purified Grade); such as Micro. Wax, Micro. Wax 2305, Micro. Wax 1135/15W (all from Ross), and such as Multiwax 180M, Multiwax ML-445, Multiwax 180W, Multiwax W-445, Multiwax W-445, Multiwax W-835, Multiwax X-145 (all from Witco/Sonneborn).

While not wishing to be bound by theory, applicants of the subject invention believe that the polymeric thickeners form a network type structure that microscopically disperses in the low viscosity oil, and that a polymeric network is formed through physical entanglement (i.e., PDMS or petrolatum in IPM or sun flower seed oil, see Type 2 and Type 3 below) or micro-domain aggregation (i.e., rubber-based block copolymers in mineral oil, Type 1 below).

Examples of detailed polymer/oil thickening compositions are specified below:

Type 1 Copolymer Thickened Mineral Oil (i.e. Commercially Available Geahlene®)

A low viscosity emollient oil thickened by a specific group of rubber-based thermoplastic block copolymers meets the above criteria. The oil/block copolymer thickening composition is claimed by U.S. Pat. No. 5,221,534 to DesLauriers et al. which patent is hereby incorporated by reference into the subject application. Under this patent, the oil/copolymer thickening compositions are currently sold/marketed under the trademark of Geahlene® by Penreco as "leave on" type skin care products, such as health and beauty aid products, which contain no lathering surfactants as used by the subject invention to promote lather.

The polymer surrounding the oil in this thickening composition is a blend of polymers used comprising at least two polymers or copolymers selected from the group consisting of diblock polymers which contain at least two thermodynamically incompatible segments, triblock copolymers, radial polymers or copolymers, multiblock polymers or copolymers, and mixtures thereof, it being required however, that at least one diblock copolymer and/or triblock copolymer be present in the composition.

The at least one diblock copolymer or said at least one triblock copolymer comprises 5% to 95% of said blend of at least two different polymers, and said diblock and triblock polymer comprises segments of styrene monomer units and other monomer units.

Preferably the blend is a mixture of diblock copolymers and triblock copolymers. By the expression thermodynamically incompatible with respect to the polymers is meant that the polymer contains at least two incompatible segments, for example at least one hard and one soft segment. In general in the diblock polymer, segments will be sequential with respect to hard and soft segments. In a triblock polymer, the ratio is two hard, one soft, two hard, one soft, etc. or a 2-1-2 copolymer. The multiblock polymers can contain any combination of hard and soft segments. As noted above, in the composition, however, there must always be present at least one of the diblock or triblock copolymers. There must also be a combination which will provide both the hard and soft characteristics necessary for the composition. These characteristics are necessary in order to provide the controlled syneresis which is an essential part of the present invention in formation of the health and beauty aid gel compositions.

In the compositions, the oil is contained within the polymer network formed by the polymer blend.

The polymers and the oil/polymers complex are described more specifically in U.S. Pat. No. 5,221,534 to DesLauriers et al., which patent is hereby incorporated by reference in the subject application.

Type 2 Silicone Oil Thickened Emollient Oils

In another embodiment of the invention, a low viscosity, non-silicone emollient oil (viscosity less than 1000 cp) thickened by high-viscosity silicone oil, such as polydimethylsiloxane (PDMS) also meet the above criteria that define the polymer thickeners selected.

The viscosity of PDMS is above 2000 cp, preferably above 5000 cp, and most preferably above 10,000 cp.

The PDMS/oil thickening system comprises 10% to 90% by wt. said PDMS, and 90% to 10% by wt. silicone soluble low viscosity emollient oils that include but are not limited to the following: diisopropyl adipate, diisopropyl sebacate, octyl isononanoate, isodecyl octanoate, diethylene glycol, isopropyl myristate, isocetyl palmitate, isopropyl isostearate, isocetyl palmitate, isostearyl palmitate, diisostearyl malate, diglyceryl isostearate, diisopropyl dimerate, diglyceryl diisostearate, and mixtures thereof.

The PDMS/oil thickening system can also comprises 20% to 95% said PDMS, and 5% to 80% by wt. low viscosity oils that are homogeneously dispersible and/or partially soluble in PDMS, which include but are not limited to: mineral oil, lanolin oil, coconut oil, jojoba oil, maleated soybean oil, castor oil, almond oil, peanut oil, wheat germ oil, rice bran oil, linseed oil, apricot pits oil, walnuts, palm nuts, pistachio nuts, sesame seeds, rape seed oil, cade oil, corn oil, peach pit oil, poppyseed oil, pine oil, soybean oil, avocado oil, sunflower seed oil, hazelnut oil, olive oil, grapeseed oil, and safflower oil, babassu oil, and mixtures thereof.

Type 3 Microcrystalline Waxes (e.g., Petrolatum) Thickened Emollient Oils

In another embodiment of the invention, microcrystalline waxes with a viscosity higher than 2000 cp, preferably higher than 5,000 cp, and most preferably higher than 10,000 cp, can also be used to thicken low viscosity emollient oils. An example of this type of thickener is petrolatum that is dominantly a natural mixture of microcrystalline waxes; an example of petrolatum is a Petrolatum from Fisher Chemical (purified grade).

The gel/oil thickening composition comprises 10% to 80% by wt. the said microcrystalline waxes and 20% to 90% by wt. low viscosity hydrophobic emollient oils (with viscosity less than 1000 cp) that can be finely dispersed and/or dissolved in the hydrocarbon gel. The oils include but are not limited to: mineral oil, lanolin oil, coconut oil, jojoba oil, maleated soybean oil, almond oil, peanut oil, wheat germ oil, rice bran oil, linseed oil, apricot pits oil, walnuts oil, palm nuts oil, pistachio nuts oil, sesame seeds oil, rape seed oil, cade oil, corn oil, peach pit oil, poppyseed oil, pine oil, soybean oil, avocado oil, sunflower seed oil, hazelnut oil, olive oil, grapeseed oil, and safflower oil, babassu oil, isopropyl myristate and mixtures thereof.

As noted above, it is the specific polymeric thickening agents which allow the low viscosity oil to deliver improved moisturization effect while providing significantly less antifoaming in comparison to the non-thickened oil or oil thickened by those crystalline thickeners, such as paraffin and polyethylene waxes, $C_{18}$–$C_{22}$ fatty acid soap and silica or silicate. As an additional advantage, the polymer/oil thickening compositions are stable in the claimed bar cleansing formulations and resist phase separation from the bulk phase during the bar processing.

(c) Structuring Aids and/or Fillers

The compositions may also contain 0.1 to 80% by wt., preferably 5 to 75% by wt. of a structurant and/or filler. Such structurants can be used to enhance the bar integrity, improve the processing properties, and enhance desired user sensory profiles.

The structurant is generally long chain, preferably straight and saturated, ($C_8$–$C_{24}$) fatty acid or ester derivative thereof; and/or branched long chain, preferably straight and saturated, ($C_8$–$C_{24}$) alcohol or ether derivatives thereof.

A preferred bar structurant is polyalkylene glycol with molecular weight between 2000 and 20,000, preferably between 3000 and 10,000. Those PEGs are commercially available, such as those marketed under the tradename of CARBOWAX SENTRY PEG8000® or PEG4000® by Union Carbide.

Other ingredients that can be used as structurants or fillers include starches, preferably water soluble starches such as maltodextrin and polyethylene wax or paraffin wax.

Structuring aids can also be selected from water soluble polymers chemically modified with hydrophobic moiety or moieties, for example, EO-PO block copolymer, hydrophobically modified PEGs such as POE(200)-glyceryl -stearate, glucam DOE 120 (PEG 120 Methyl Glucose Dioleate), and Hodag CSA-102 (PEG-150 stearate), and Rewoderm® (PEG modified glyceryl cocoate, palmate or tallowate) from Rewo Chemicals.

Other structuring aids which may be used include Amerchol Polymer HM 1500 (Nonoxynyl Hydroethyl Cellulose).

(D) Optional ingredients

In addition, the bar compositions of the invention may include 0 to 15% by wt. optional ingredients as follows:
perfumes; sequestering agents, such as tetrasodium ethylenediaminetetraacetate (EDTA), EHDP or mixtures in an amount of 0.01 to 1%, preferably 0.01 to 0.05%; and coloring agents, opacifiers and pearlizers such as zinc stearate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4'trichlorodiphenylether (DP300); preservatives such as dimethyloldimethylhydantoin (Glydant XL1000), parabens, sorbic acid etc.

The compositions may also comprise coconut acyl mono- or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic polymers as conditioners which may be used include Quatrisoft LM-200 Polyquaternium-24, Merquat Plus 3330—Polyquaternium 39; and Jaguar® type conditioners.

Polyethylene glycols as conditioners which may be used include:

| Polyox | WSR-205 | PEG 14M, |
|---|---|---|
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

The present invention is set forth in greater detail in the examples which follow. The examples are for illustration purposes only and are not intended to limit the scope of the claims in any way.

All percentages in the examples and specification, unless indicated otherwise, are intended to be percentages by weight.

EXAMPLES

Methodology (A) Lather Assessments
Ross-Miles Method

Foam height was measured by the Ross-Miles method (for detail, see J. Ross and G. D. Miles, Am. Soc. for Testing Materials, Method D1173-53, Philadelphia, Pa., 1953). In this invention, 200 ml of a test solution comprised of 0.5% by wt. total surfactant concentration contained in a pipette of specified dimensions with a 2.9 mm I.D. orifice are allowed to fall 90 cm onto 50 ml of the same solution contained in a cylindrical vessel maintained at a given temperature (40° C.) by means of a water jacket. The height of the foam produced in the cylindrical vessel is read immediately after all the solution has run out of the pipette ("initial foam height") and then again after given amount of time (foam aging time).

Cylinder-Shaking Method

Foam volume was also tested using a cylinder-shaking method. Forty grams of solution (2.5% by wt. total surfactant concentration) was put in a 250 ml PYREX cylinder with cap. Foam was generated by shaking the cylinder (by a trained evaluator) for 0.5 minute. After the foam settled for 2.5 minutes, the foam height was measured.

(B) Processing of Bar Containing the Polymer-Thickened Oils

Cast-Melt

Bars containing the thickened oils were prepared by a cast melt process. First, the components comprising the pre-thickened oil composition and a co-solvent/structurant (i.e., PEG or fatty acid) were mixed together at 80°–120° C. a 500 ml beaker for 30 to 60 minutes using a overhead stir. Then the rest of the components were added, and the water level was adjusted to approximately 10–15 wt.%. The batch was covered to prevent moisture loss and was mixed for about 15 to 45 minutes. Then the cover was removed, and the mixture was allowed to dry. The moisture content of the samples taken at different times during the drying stage and was determined by Karl Fisher titration with a turbo titrator. At the final moisture level (~5%), the mixture in the beaker (in the form of a free-flow liquid) was dropped into bar molds and was allowed to be cooled at room temperature for four hours. Upon solidification, the mixture was casted in the bar molds into bars.

Oil Chipping/Coextrusion

This is a preferred method that tended to preserve the pre-thickened oils as discrete large droplets (desirable for skin deposition) in the continuous bar matrix. First, the pre-thickened oil composition and a structurant and/or cosolvent (e.g., PEG, hydrophobically modified PEG, EO-PO copolymers or fatty acid) were mixed together at 80°–120° C. in a 500 ml beaker for 30 to 60 minutes using a overhead stir. Then the resulting mixed mass (a homogenous viscous liquid)-was dropped onto a heated applicator roll and then was chipped over a chill roll. These chill roll chips were mixed with the chips that comprised the rest of the bar compositions and then were plodded together under vacuum in a Weber Seelander duplex refiner with screw speed at about 20 RPM. The nose cone of the plodder was heated to 45° C. to 50° C. The cut billets were stamped into bars using a Weber Seelander L4 hydraulic press with a nylon die in place.

Cavity Filling

Cavity filling is a preferred method that allow the pre-thickened oils to be directly transferred from bar onto skin in the form of large droplets. First, the pre-thickened oil composition and a structurant and/or cosolvent (e.g., PEG, hydrophobically modified PEG, EO-PO copolymers or fatty acid) were mixed together at 80° C.–120° C. in a 500 ml beaker for 30 to 60 minutes using a overhead stir. Then the molten mixture (80° C.–120° C.) was dropped (or injected by a pump) into the cavity (i.e., holes, stripes, trenches, or any part of the bar shape) of a solid bar base (at 20° C.) comprising the rest of the total bar composition. Upon solidification by cooling to room temperature, the molten mixture turned into a solid domain affixed to the rest of the bar base.

Example 1
Bar composition prepared by the cavity filling method
Invention

First, 10% by wt. Geahlene® 1600 (ex. Penreco) was homogeneously mixed with 90% by wt. molten PEG8000 (ex. Union Carbide) at a temperature of 95° C. for about 40 minutes. Then the resulting viscous clear liquid was dropped into a rectangular shaped cavity (4 cm/2 cm/1 cm) of a commercial Dove Beauty Bar®. Upon cooling at room temperature for about 2 hours, the viscous liquid of Geahlene/PEG in the Dove cavity turned into a solid domain that is affixed to the surrounding Dove. The bar provides rich and creamy lather and smooth and oily skin feel. Additionally, 10% of the bar materials (comprising 5% Dove material plus 5% cavity material containing Geahlene® 1600) deliver large size, high viscosity oil droplets in water, which is desirable for the oil deposition onto skin and skin moisturization (as seen, for example in World Patent applications WO 94/01084 and WO 94/01085).

Comparative

In contrast, if the non-thickened low viscosity oils (i.e., viscosity below 1000 cp), such as low viscosity silicone oil, benzyl laurate, and mineral oil are mixed with the molten PEG, they can readily phase separate from the molten PEG8000 at a temperature of 95° C. to 120° C. Therefore, those non-thickened low viscosity oils may cause processing difficulties. Further, 10% non-thickened mineral oil (from FisherChemical) was used to replace the Geahlene® in the above cavity-filling bar under the same bar processing conditions. 10% of the bar materials (comprising 5% Dove material plus 5% cavity material containing non-thickened mineral oil) in water delivered a large pool of oil which separated from the aqueous liquor and left very small amount of small oil droplets in the liquor, and this is not desired for the oil deposition onto skin.

Example 2
Bar composition prepared by the oil chipping/coextrusion method

First, 10% by wt. Geahlene® 1600 (ex. Penreco) was homogeneously mixed with 90% molten PEG8000 (ex. Penreco) at 95° C. for about 40 minutes. Then the resulting viscous, clear liquid was chill rolled to flakes of bright white color.

Then these Geahlene/PEG chill roll chips were mixed with flakes/chips of commercial Dove® in a 4:6 weight ratio. Then the mixed chips were coextruded and stamped into Dove shaped skin cleansing bars that provide rich and creamy lather and smooth, moisturizing skin feel.

Alternatively, these Geahlene/PEG chill roll chips were mixed with the base flakes/chips of any compositions shown in Table 3 (A, or B, or C) in 4:6 weight ratio. Then the mixed chips were coextruded and stamped into rectangular shaped bars which provide rich and creamy lather and smooth, oily skin feel.

TABLE 3

The base flake compositions to be mixed with the Geahlene ®/ PEG (1:9 w/w) chips

| Flake Composition | A (% wt.) | B (% wt.) | C (% wt.) |
|---|---|---|---|
| sodium cocoyl isethionate (from DEFI*) | 45.0 | 50.0 | 0 |
| cocoamido propyl betaine | 7.0 | 8.3 | 0 |
| stearic-palmitic acid | 19.0 | 21.0 | 0 |
| sodium stearate | 8.0 | 11.0 | 0 |
| PEG8000** | 10.6 | 0 | 0 |
| tallow/coco (80/20 w/w) fatty acid soap | 2.0 | 2.0 | 86.2 |
| Perfume | 0.3 | 0.3 | 0.3 |
| Titanium dioxide | 0.4 | 0.4 | 0 |
| EDTA | 0.1 | 0.1 | 0 |
| EDHP | 0.1 | 0.1 | 0 |
| sodium chloride | 0.5 | 0.5 | 0.5 |
| water | 7 | 7 | 13.0 |

*DEFI: directly esterified fatty acid isethionate, which is a mixture containing about 74% by weight of fatty acid isethionates, 23% stearic-palmitic acid and small amounts of other materials, manufactured by Lever Brothers Co., U.S.
**PEG8000: polyoxyethylene glycol with mean molecular weight at 8000.

Example 3
Bar compositions prepared by the cast melt method
Total Bar compositions (Formulation CM-I and CM-II) are shown in Table 4. First, by using a overhead stir, the pre-thickened oil (i.e., Geahlene, or Silicone/IPM, or Petrolatum/Sun flower seed oil) were mixed with molten PEG8000 at a temperature of 95° C. for about 40 minutes or until the mix turned into a homogenous viscous liquid. Then rest of the compositions were added into the liquid for about 1 to 2 hours until a homogenous mixing was achieved. Then at the final moisture level (~5%), the mixture in the beaker (in the form of a free-flow liquid) was dropped into bar molds and was allowed to be cooled at room temperature for four hours. Upon solidification, the mixture was casted in the bar molds into bars. These bars provides rich and creamy lather and smooth, oil skin feel.

TABLE 4

Cast melt bar compositions containing the pre-thickened emollient oils

| Compositions | Formulation CM-I (% wt.) | Formulation CM-II (% wt.) |
|---|---|---|
| sodium cocoyl isethionate | 27.1 | 28.5 |
| cocoamidopropyl betaine | 5.0 | 5.0 |
| PEG8000 | 38.0 | 10.0 |
| sodium stearate | 5.0 | 10.0 |
| palmitic/stearic acid | 8.4 | 14.5 |
| paraffin wax | 0 | 3.0 |
| glyceryl stearate (Tego Care) | 0 | 5.0 |
| propylene glycol | 0 | 5.0 |
| Geahlene ® 1600/IPM 1:1 (w/w) mixture (pre-thickened oil) | 10.0 | 0 |
| Silicone (Dow Corning 200 ®, viscosity = 100,000 cp)/IPM 1:1 mixture (pre-thickened oil) | 0 | 5.0 |
| Petrolatum (viscosity greater than 100,000 cp)/sunflower seed oil 1:1 mixture (pre-thickened oil) | 0 | 5.0 |
| misc. salts (i.e, sodium chloride, sodium isethionate | 1.5 | 0 |
| water | 5.0 | 5.5 |

Example 4

The impact of Geahlene and Geahlene derivatives on the lather of personal washing aqueous liquors In order to study the impact of Geahlene and Geahlene derivatives on lather, an aqueous surfactant liquor (L-1 in Table 5) that is relevant to personal washing condition (i.e., surfactant concentration ranges between 0.2 and 5% wt. in water) was made. L-1 loaded with Geahlene or Geahlene/IPM resulted in liquor L-2 and L-3 respectively. For the purpose of comparison, non-thickened isopropylmyristate (IPM) was included in L-1 and resulted in L-4. By adequate mixing with an overhead mixer, all those aqueous liquors turned into milky dispersions during the lather testing.

According to results of the Ross-miles foam height tests (Table 6), L-2 and L-3 showed foam heights that were comparable to that of L-1. However, L-4 containing the non-thickened IPM had a significantly lower foam height after six minutes of foam aging.

TABLE 5

Compositions of surfactant aqueous liquors containing thickened oils

| Composition | L-1 (% wt.) base | L-2 (% wt.) invention | L-3 (% wt.) invention | L-4 (% wt.) comparative |
|---|---|---|---|---|
| Coco amido propyl betaine (trade name: F40, from Goldschmidt) | 0.250 | 0.250 | 0.250 | 0.250 |
| Sodium laurylether (3EO) sulfate (trade name: CS-330, from Stepan) | 0.125 | 0.125 | 0.125 | 0.125 |
| Sodium cocoyl isethionate (Jordapon, from Rhone Poulenc) | 0.125 | 0.125 | 0.125 | 0.125 |
| Geahlene ® 750 | 0 | 0.625 | 0 | 0 |
| Pre-thickened Geahlene 1600/Isopropyl myristate (1:1 w/w) | 0 | 0 | 0.5 | 0 |
| non-thickened isopropyl myristate | 0 | 0 | 0 | 0.25 |
| water | add up to 100% wt. | add up to 100% wt. | add up to 100% wt. | add up to 100% wt. |

TABLE 6

Ross-Miles Foam Height for surfactant aqueous liquors containing the thickened oils

| Foam Aging Time (minutes) | Foam Height (cm) L-1 (base) | Foam Height (cm) L-2 (invention) | Foam Height (cm) L-3 (invention) | Foam Height (cm) L-4 (comparative) |
|---|---|---|---|---|
| 0.8 | 18 | 18 | 18 | 17 |
| 1.7 | 17 | 18 | 18 | 17 |
| 2.5 | 17 | 17 | 18 | 16 |
| 4.1 | 17 | 17 | 17 | 16 |
| 6.2 | 16 | 17 | 17 | 15 (also formed thin foam, not desired) |
| 8.0 | 16 | 17 | 17 | 13 (thin foam) |
| 9.4 | 16 | 17 | 16 | 12 (thin foam) |
| 10 | 16 | | 16 | 12 (thin foam) |
| 12 | 16 (still creamy foam desired) | | 16 (still creamy foam, desired) | 10 (thin foam) |

Example 5

The impact of silicone or petrolatum thickened oils on lather

In order to study the impact of Silicone and petrolatum thickened oils on lather, an aqueous surfactant liquor (L-5 in Table 7) that is relevant to personal washing condition (i.e., surfactant concentration ranges between 0.2 and 5% wt. in water) was made. L-5 loaded with silicone (viscosity at 60,000 cp) or petrolatum (from FisherChemical) thickened IPM resulted in liquor L-6 and L-7 respectively. For the purpose of comparison, isopropylmyristate (IPM) thickened by aluminum stearate (a crystalline thickener) was included in L-1 and resulted in L-8. By adequate mixing with an overhead mixer, all those aqueous liquors turned into milky dispersions during the lather testing.

According to results of the cylinder shaking tests (Table 8), L-6 and L-7 (thickened with the thickeners of the invention) generated lather volumes that were significantly more than that of L-8, which contained an oil thickened by a crystalline thickener.

TABLE 7

Aqueous surfactant liquors that contain the thickened oils of the invention.

| Compositions | L-5 (% wt.) (base) | L-6 (% wt.) (invention) | L-7 (% wt.) (invention) | L-8 (comparative) |
|---|---|---|---|---|
| sodium cocoyl isethionate | 0.625 | 0.625 | 0 | 0 |
| cocoamido propyl betaine | 1.25 | 1.25 | 0 | 0 |
| sodium laurylether sulfate (3EO) | 0.625 | 0.625 | 0 | 0 |
| 1:1 w/w IPM/PDMS | 0 | 2.49 | 0 | 0 |
| 1:1 w/w sunflower seed oil/PDMS | 0 | 0 | 2.49 | 0 |
| 1:9 w/w Aluminum stearate/IPM | 0 | 0 | 0 | 2.49 |
| water | to 100% by wt. | to 100% by wt. | to 100% by wt. | to 100% by wt. |

TABLE 8

Comparison of the lather volume of Composition L6 to L8

| Composition | Lather Volume (ml) generated from the Cylinder-shaking Method |
|---|---|
| L6 | 172 |
| L-7 | 181 |
| L-8 | 117 |

We claim:

1. A skin cleansing bar composition comprising:
   (a) 10% to 95% by wt. of a surfactant selected from the group consisting of anionic surfactants, cationic surfactants, amphoteric surfactants, nonionic surfactants and mixtures thereof;
   (b) 0.5% to 45% by wt. total composition of a pre-thickened oil composition having a viscosity above 2000 centipoise (cp);
   (c) 0.1 to 80% by wt. total composition of a structuring aid or inert filler selected from the group consisting of long chain ($C_8$–$C_{24}$), branched or unbranched, saturated or unsaturated, fatty acid; ester derivatives of said fatty acid; $C_8$–$C_{24}$ branched or unbranched saturated or unsaturated alcohol; ether derivatives of said alcohol; polyalkylene glycol having molecular weight between 2000 and 20,000; water soluble starches; polyethylene wax; paraffin wax; water soluble polymers chemically modified with hydrophobic moiety or moieties; and mixtures thereof;
   wherein said pre-thickened oil composition (b) comprises
      (i) a hydrophobic agent having a viscosity of less than 1000 cp; and
      (ii) a polymeric non-antifoaming thickener compound;
   wherein by non-antifoaming is meant that the composition containing the pre-thickened oil composition (b) provides a foam height of seven cm or greater after two minutes of foam aging, as tested by a foam measuring method known as the Ross-Miles method,
   wherein said non-antifoaming thickener (b)(ii) is selected such that:
      (A) a hydrophobicity of the polymeric thickener is such that said polymeric thickener has a solubility of less than 1% by wt. when measured in water at 25° C.;
      (B) an oil miscibility and/or dispersibility of the thickener is such that, upon mixing with said low viscosity hydrophobic agent (b)(i), the pre-thickened oil composition which forms is a homogeneously thickened oil having a viscosity of greater than 2000 cp and which does not have layer separation; and
      (C) crystalline materials (excluding microcrystalline waxes) present in the thickener, if any, are present in an amount less than 20% by wt. of said thickener, and wherein non-crystaline materials selected from the group consisting of gels, amorphous solids, microcrystalline waxes and mixtures thereof, are present in the thickener in an amount greater than 80% by wt of said thickener.

2. A composition according to claim 1, wherein (b)(i) is selected from the group consisting of mineral oil, isopropyl myristate, isopropyl palmitate, silicones, benzoate esters and mixtures thereof, and the polymeric thickener (b)(ii) is a blend of at least two different polymer members selected from the group consisting of diblock copolymers, triblock copolymers, radial block copolymers and multiblock copolymers, with the proviso that there be contained in the composition at least one diblock copolymer or at least one triblock copolymer, with said at least one diblock copolymer or said at least one triblock copolymer comprising 5 to 95 wt. % of said blend of at least two different polymers, said diblock and triblock polymers comprising segments of styrene monomer units and rubber monomer units.

3. A composition according to claim 1, wherein (b)(i) comprises 10% to 90% of a silicone soluble hydrophobic agent selected from the group consisting of diisopropyl adipate, diisopropyl sebacate, octyl isononanoate, isodecyl octanoate, diethylene glycol, isopropyl myristate, isocetyl palmitate, isopropyl isostearate, isocetyl palmitate, isostearyl palmitate, diisostearyl malate, diglyceryl isostearate, diisopropyl dimerate, diglyceryl diisostearate, and mixtures thereof; and (b)(ii) comprises 10% to 90% by wt. silicone oil having viscosity greater than 2000 cps.

4. A composition according to claim 3, wherein said silicone oil has a viscosity greater than 5,000 cp.

5. A composition according to claim 3, wherein said silicone oil has a viscosity greater than 10,000 cp.

6. A composition according to claim 1, wherein (b)(i) comprises 5% to 80% by wt. of a hydrophobic agent with a viscosity less than 1000 cp selected from the group consisting of mineral oil, glyceryl, sorbitol, lanolin oil, coconut oil, jojoba oil, maleated soybean oil, castor oil, almond oil, peanut oil, wheat germ oil, rice bran oil, linseed oil, apricot pits oil, walnuts, palm nuts, pistachio nuts, sesame seeds, rape seed oil, cade oil, corn oil, peach pit oil, poppyseed oil, pine oil, soybean oil, avocado oil, sunflower seed oil, hazelnut oil, olive oil, grapeseed oil, and safflower oil, babassu oil, and mixtures thereof; and (b)(ii) comprises 20% to 95% by wt. silicone oil having a viscosity greater than 2000 cps.

7. A composition according to claim 6, wherein (b)(ii) is a silicone oil having a viscosity greater than 10,000 cp.

8. A composition according to claim 6, wherein (b)(i) comprises 20% to 60% by wt. of the composition, (b)(ii) comprises 40% to 80% of the composition and (b)(ii) has a viscosity greater than 10,000 cp.

9. A composition according to claim 1, wherein (b)(i) comprises a hydrophobic agent with viscosity less than 1000 cp selected from the group consisting of mineral oil, sorbitol, lanolin oil, coconut oil, jojoba oil, maleated soybean oil, castor oil, almond oil, peanut oil, wheat germ oil, rice bran oil, linseed oil, apricot pits oil, walnuts, palm nuts, pistachio nuts, sesame seeds, rape seed oil, cade oil, corn oil, peach pit oil, poppyseed oil, pine oil, soybean oil, avocado oil, sunflower seed oil, hazelnut oil, olive oil, grapeseed oil, and safflower oil, Shea butter, babassu oil, isopropyl myristate and mixtures thereof; and (b)(ii) comprises 10% to 80% by wt. microcrystalline waxes having viscosity greater than 2000 cp.

10. A composition according to claim 9, wherein the microcrystalline wax is petrolatum having a viscosity greater than 10,000 cp.

11. A composition according to claim 1, wherein the skin cleansing composition comprises 25% to 70% by wt. of a surfactant selected from the group consisting of anionic surfactants, cationic surfactants, amphoteric surfactants, nonionic surfactants and mixtures thereof.

12. A composition according to claim 1, wherein the bar composition further comprises 0 to 5% by wt. perfumes; 0.01 to 1% by wt. sequestering agents; and 0 to 2% of an ingredient selected from the group consisting of coloring agents, opacifiers, pearlizers and mixtures thereof.

13. A composition according to claim 1, wherein the composition further comprises 0 to 3% by wt. antimicrobial agent.

14. A composition according to claim 13, wherein the antimicrobial is 2-hydroxy-4,2'4'trichlodiphenyl ether.

15. A composition according to claim 1, wherein said composition further comprises a preservative.

16. A composition according to claim 15, wherein the preservative is selected from the group consisting of dimethyloldimethylhydantion, parabens and sorbic acid.

17. A composition according to claim 1, wherein the composition further comprises 0 to 3% by wt. antioxidants.

18. A composition according to claim 17, wherein the antioxidant is butylated hydroxytoluene.

19. A composition according to claim 1, wherein the composition further comprises 0 to 5% by wt. cationic conditioners.

20. A composition according to claim 1, wherein the polyalkylene glycol is selected from nonionic polyethylene glycols having molecular weight between 2000 and 20,000 Dalton.

21. A composition according to claim 1, wherein the composition further comprises 0 to 10% by wt. nonionic polyethylene glycols having molecular weight greater than 50,000 Dalton.

22. A composition according to claim 1, wherein the composition further comprises exfoliants.

23. A composition according to claim 22, wherein said exfoliants are selected from the group consisting of polyoxyethylene beads, walnut shells and apricot seeds.

24. A composition according to claim 1, wherein the pre-thickened oil composition has a viscosity greater than 5000 cp at a temperature of 25° C.

25. A composition according to claim 1, wherein the skin cleansing composition contains said pre-thickened oil composition having a viscosity greater than 10,000 cp at a temperature of 25° C.

26. A composition according to claim 1, wherein the skin cleansing composition contains 5% to 25% by wt. of said pre-thickened oil composition.

27. A composition according to claim 1, wherein said bar composition containing said pre-thickened oil (first bar) provides a foam height that is at least 30% greater than that provided by a comparative bar composition containing a percentage and amount of low viscosity oil (viscosity less than 1000 cp) identical to that used in said first bar, but wherein the oil in the comparative bar has been pre-thickened by crystalline thickeners, selected from polyethylene or paraffin waxes, $C_{18}$–$C_{22}$ fatty acid soap and fumed silica wherein said foam height test is conducted using Ross-Miles method of measuring foam and foam height is measured after two minutes.

* * * * *